United States Patent
Lindsay et al.

(10) Patent No.: US 9,766,248 B2
(45) Date of Patent: Sep. 19, 2017

(54) CHEMISTRY, SYSTEMS AND METHODS OF TRANSLOCATION OF A POLYMER THROUGH A NANOPORE

(71) Applicant: ARIZONA BOARD OF REGENTS ACTING FOR AND ON BEHALF OF ARIZONA STATE UNIVERSITY, Scottsdale, AZ (US)

(72) Inventors: Stuart Lindsay, Phoenix, AZ (US); Peiming Zhang, Gilbert, AZ (US); Sudipta Biswas, Tempe, AZ (US)

(73) Assignee: Arizona Board of Regents of behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/893,413

(22) PCT Filed: May 23, 2014

(86) PCT No.: PCT/US2014/039407
§ 371 (c)(1),
(2) Date: Nov. 23, 2015

(87) PCT Pub. No.: WO2014/190299
PCT Pub. Date: Nov. 27, 2014

(65) Prior Publication Data
US 2016/0146828 A1  May 26, 2016

Related U.S. Application Data

(60) Provisional application No. 61/826,855, filed on May 23, 2013.

(51) Int. Cl.
*G01N 15/06* (2006.01)
*G01N 33/00* (2006.01)
(Continued)

(52) U.S. Cl.
CPC ......... *G01N 33/6818* (2013.01); *C07K 1/107* (2013.01); *G01N 33/48721* (2013.01)

(58) Field of Classification Search
CPC ......... G01N 15/06; G01N 33/00; G01N 33/48
(Continued)

(56) References Cited

U.S. PATENT DOCUMENTS 5,066,716 A     11/1991  Robey et al.
6,210,896 B1 *  4/2001   Chan ........................... 435/6.19
(Continued)

FOREIGN PATENT DOCUMENTS

WO    2008124706 A2    10/2008
WO    2009117517        9/2009
(Continued)

OTHER PUBLICATIONS

Nivala et al., Unfoldase-mediated protein translocation through an α-hemolysin nanopore, Nature Biotechnology, Mar. 2013, 31(3):247-250.
(Continued)

*Primary Examiner* — Brian J Sines
(74) *Attorney, Agent, or Firm* — Cooley LLP; Ivor Elrifi; Brian P. Hopkins

(57) ABSTRACT

Embodiments disclosed herein are directed to recognition tunneling systems, methods and devices, and more particularly, to chemical reactions for selectively labeling proteins and peptides and placing protein and/or peptides into, or onto a nanopore formed in a solid support and threading such in and/or through the nanopore, with such nanopores, in some embodiments, including a molecular motor to pull or otherwise force the protein/peptide through the nanopore.

7 Claims, 3 Drawing Sheets

(51) Int. Cl.
*G01N 33/48* (2006.01)
*G01N 33/68* (2006.01)
*C07K 1/107* (2006.01)
*G01N 33/487* (2006.01)

(58) Field of Classification Search
USPC ....... 422/50, 68.1, 502, 503; 436/43, 86, 89; 977/700, 902, 920, 953, 957, 958
See application file for complete search history.

(56) References Cited

U.S. PATENT DOCUMENTS

| | | | |
|---|---|---|---|
| 6,355,420 | B1* | 3/2002 | Chan ........................... 435/6.12 |
| 7,410,564 | B2* | 8/2008 | Flory ......................... 205/777.5 |
| 7,744,816 | B2* | 6/2010 | Su et al. ...................... 422/68.1 |
| 2003/0207326 | A1* | 11/2003 | Su et al. ........................ 435/7.1 |
| 2004/0029792 | A1 | 2/2004 | Beraud et al. .................. 514/12 |
| 2005/0053591 | A1* | 3/2005 | Pun .............................. 424/94.1 |
| 2010/0084276 | A1 | 4/2010 | Lindsay |
| 2012/0288948 | A1 | 11/2012 | Lindsay et al. |
| 2014/0174927 | A1* | 6/2014 | Bashir et al. ................. 204/452 |
| 2014/0255921 | A1* | 9/2014 | Moysey et al. ................ 435/6.1 |
| 2015/0010935 | A1 | 1/2015 | Lindsay et al. |
| 2015/0337366 | A1* | 11/2015 | Davis et al. ................. 422/68.1 |

FOREIGN PATENT DOCUMENTS

| | | |
|---|---|---|
| WO | 2009117522 A2 | 9/2009 |
| WO | 2010042514 A1 | 4/2010 |
| WO | 2013151756 A1 | 10/2013 |
| WO | 2014138253 A1 | 9/2014 |
| WO | 2014165168 | 10/2014 |
| WO | 2014190299 A2 | 11/2014 |
| WO | 2014190299 A3 | 1/2015 |

OTHER PUBLICATIONS

Rodriguez et al., Multistep protein unfolding during nanopore translocation, Nature Nanotechnology, Apr. 2013, 8(4):288-295.
Kolb et al., Click Chemistry: Diverse Chemical Function from a Few Good Reactions, Angew. Chem. Int. Ed., Jun. 2001, 40(11):2004-2021.
Hall et al., Hybrid pore formation by directed insertion of alpha hemolysin into solid-state nanopores, Nature Nanotechnology, Dec. 2010, 5(12):874-877.
Mohammad et al., Controlling a single protein in a nanopore through electrostatic traps, J. Am. Chem. Soc., Mar. 2008, 130(12):4081-4088.
Lu et al., Click chemistry functionalized polymeric nanoparticles target corneal epithelial cells through RGD-cell surface receptors, Bioconjugate Chem., Jan. 2009, 20(1):87-94.
Pressly et al., Rapid synthesis of block and cyclic copolymers via click chemistry in the presence of copper nanoparticles, Journal of Polymer Science, Part A: Polymer Chemistry, Feb. 2011, 49(3):814-819.
Huang et al., Identifying single bases in a DNA oligomer with electron tunnelling, Nature Nanotechnology, Dec. 2010, 5(12):868-873.
Lindsay et al., Recognition tunneling, Nanotechnology, Jul. 2010, 21(26):262001-262013.
Liang et al., Synthesis, Physicochemical Properties, and Hydrogen Bonding of 4(5)-Substituted 1-H-Imidazole-2-carboxamide, a Potential Universal Reader for DNA Sequencing by Recognition Tunneling, Chemistry—A European Journal, May 2012, 18(19):5998-6007.
Lawson et al., Transport in molecular junctions with different metallic contacts, Physical Review B—Condensed Matter and Materials Physics, Sep. 2006, 74(12):125401.
Chang et al., Gap distance and interactions in a molecular tunnel junction, J. Am. Chem. Soc., Sep. 2011, 133(36):14267-14269.
Hempel, An orientation to Edman chemistry, Modern Protein Chemistry (Howard and Brown), 2002, 103-122, CRC Press.
Chang et al., Chemical recognition and binding kinetics in a functionalized tunnel junction, Nanotechnology, Jun. 2012 23(23):235101.
Chang et al., LIBSVM: A Library for support vector machines, LIBSVM: A Library for support vector machines, Apr. 2011, 2(3): Article 27.
Chen et al., Subfemtomole level protein sequencing by Edman degradation carried out in a microfluidic chip, Chemical Communications, 2007, 24:2488-2490.
Chen et al., Optimization of microfabricated nanoliter-scale solid-phase extraction device for detection of gel-separated proteins in low abundance by matrix-assisted laser desorption/ionization mass spectrometry, Rapid Communications in Mass Spectrometry, Jan. 2007, 21(1):35-43.
Tuchband et al., Insulated gold scanning tunneling microscopy probes for recognition tunneling in an aqueous environment, Rev. Sci. Instrum., Jan. 2012, 83(1):015102-015102-4.
Louwagie et al., Introducing AAA-MS, a rapid and sensitive method for amino acid analysis using isotope dilution and high-resolution mass spectrometry, J. Proteome Res., Jul. 2012, 11(7):3929-3936.
Rosnack et al., C-terminal sequencing of peptides using electrospray ionization mass spectrometry, Rapid Commun. Mass Spectrom., Nov. 1992, 6(11):637-640.
Walker et al., C-Terminal Sequence Analysis with Carboxypeptidase Y, The Protein Protocols Handbook (Walker), 1996, 569-571, Ed. Humana Press Inc.
Yan-Fei et al., Development of C-terminal Sequencing Analysis of Protein and Peptide, Chinese Journal of Analytical Chemistry, Dec. 2007, 35(12):1820-1826.

* cited by examiner

US 9,766,248 B2

CHEMISTRY, SYSTEMS AND METHODS OF TRANSLOCATION OF A POLYMER THROUGH A NANOPORE

RELATED APPLICATIONS

This application is a U.S. national stage application of International Application No. PCT/US2014/039407, filed on May 23, 2014, and claims benefit under 35 U.S.C. §119(e) of U.S. provisional patent application No. 61/826,855, filed on May 23, 2013, the entire disclosure of which is herein incorporated by reference.

The contents of the text file submitted electronically herewith are incorporated herein by reference in their entirety: A computer readable format copy of the Sequence Listing (filename: ARIZ_013_N01US_SeqList_ST25.txt, date recorded: Jan. 29, 2016, file size 6 kilobytes).

STATEMENT REGARDING FEDERALLY SPONSORED RESEARCH & DEVELOPMENT

This invention was made with government support under R01 HG006323 awarded by the National Institutes of Health. The government has certain rights in the invention.

FIELD OF THE DISCLOSURE

Embodiments disclosed herein are directed to recognition tunneling systems, methods and devices, and more particularly, to chemical reactions for selectively labeling N-termini of proteins and peptides, to address problems with analyzing and sequencing unknown proteins, as well as embodiments directed to placing a protein into, or onto a nanopore formed in a solid support (which may otherwise be referred to as a support structure).

BACKGROUND

In PCT application no. US2014/024630 ("the '630 application"), entitled, "Systems, Devices and Methods for Translocation Control," the entire disclosure of which is incorporated herein by reference, a general chemical approach to connecting a polyion onto the N-terminus of any protein is disclosed. In some of the disclosed embodiments thereof, one step of such a process is functionalizing the N-terminus of a protein with an alkyne moiety for subsequent ligation to any azide containing group by conventional "click" chemistry.[3] In some of the disclosed embodiments of the '630 application, this step takes place at the N-terminus, without any side reactions, for example, with ε-amino group (a primary amine) of lysine. As disclosed in the '630 application, this may be achieved using 3-(2-propynyl) succinic anhydride at pH 7.6 in a sodium acetate buffer.

SUMMARY OF THE DISCLOSED EMBODIMENTS

Some embodiments of the present disclosure are directed to improvements in connecting a polyion onto the N-terminus of a protein, by way of chemical reaction. In some embodiments, close to a 100% yield of the desired product may be achieved. In some embodiments, a protein motor, specifically, an unfoldase, a protein configured to pull or otherwise force a protein through an orifice, in some embodiments, one amino acid residue at a time, is provided which can be used with solid-state nanopores. A solid-state nanopore, in the disclosed embodiments, corresponds to an opening/hole fabricated in a support structure. In some embodiments, the new reaction(s) for connecting polyion onto the N-terminus of a protein are combined with a manner of use of a protein motor (i.e., a molecular motor) with nanopores, to achieve single molecule protein sequencing, for example.

With respect to a protein (molecular) motor, docking a protein into a nanopore, at times and depending upon variables, may be challenging.[4] For example, this can be the case with a membrane protein pore, alpha hemolysin. Specifically, such a protein pore often self-assembles into the hydrophobic interior of a lipid bilayer because of hydrophobic residues on the outside of the barrel of the pore. For the similar reasons, the hydrophobic external surface of the pore may be driven onto a surface (e.g., silicon or silicon nitride) at a water-surface interface. Since the surface generally cannot yield like a lipid bilayer can, the protein is often destroyed in the process. However, the situation is different when the protein in question is soluble, with a hydrophilic exterior. To that end, it has been found that these proteins are not denatured when in close proximity to a silicon or silicon nitride surface. Accordingly, in some embodiments, these proteins can be threaded onto a polymer that is, in turn, threaded into a nanopore.

In some embodiments, a method for preparing a modified protein or peptide for enabling identification of the protein or peptide in an identification or sequencing apparatus, the modified protein or peptide having a reactive alkyne group at the N terminus of the protein or peptide, the method comprising one or more (and preferably all) of the following: dissolving a protein sample into an aqueous acetate buffer to produce a first solution, adjusting the pH of the first solution to between about 5.0 and about 7.6, dissolving pentynoic anhydride in acetonitrile to a concentration of between about 1 and about 100 mM to produce a second solution, and mixing the first solution and the second solution at about 0° C. and maintaining the mixture at about 0° C. for between about 10 minutes to about 5 hours.

In some embodiments, a modified protein or peptide is presented, which is prepared by the process noted above. With the modified protein or peptide, the reactive alkyne group is provided only at the N terminus of the protein or peptide.

In some embodiments, a method for preparing a modified protein or peptide for enabling identification of the protein or peptide in an identification or sequencing apparatus, the modified protein or peptide having a reactive bromoacetyl group at the N terminus of the protein or peptide, is provided. The method comprises one or more (and preferably all) of the following: dissolving a protein sample into an aqueous acetate buffer to produce a first solution, adjusting the pH of the first solution between about 5.0 and about 7.6, dissolving bromoacetic acid in acetonitrile to a concentration of between about 1 and about 100 mM to produce a second solution, and mixing the first solution and the second solution at about 0° C. and maintaining the mixture at about 0° C. for between about 10 minutes to about 5 hours.

In some embodiments, a modified protein or peptide is provided which is prepared by the process noted above.

In some embodiments, a modified protein or peptide is provided, produced by employing pentynoic anhydride, or bromoacetyl anhydride to place an alkyne or a bromoacetyl group, respectively, at the N terminus of the protein or peptide without modifying amino acid residues in the protein or peptide.

In some embodiments, a reagent kit for modifying a protein or peptide is provided, where the kit comprises a reagent for reacting with the N-terminus of the protein or peptide, and a polymer containing at least one charged residue and terminated in a chemical group for reacting with the peptide or protein after it has been modified with the reagent. In such kits, the reagent may comprise an anhydride containing a functional group. Moreover, in such embodiments, the ionic polymer may be a peptide sequence including one or more charged residues.

In such reagent kits the peptide may contain a targeting motif for threading a molecular motor.

In some embodiments, a protein or peptide terminated in a natural N-terminus with a peptide is provided, where the peptide is disordered and carries one or more charged residues in the pH range of about 3 to about 8, for example.

In some embodiments, a protein or peptide terminated in a natural N terminus with a peptide is provided, where the peptide is disordered and carries one or more charged residues in the pH range of about 3 to about 8, for example, and may be terminated in an amino acid sequence for threading a molecular motor.

In some embodiments, a method for identifying and/or sequencing single protein or peptide molecules is provided, where the method may comprise one or more of (and preferably all): attaching a polymer containing one or more charged residues to one end of the protein or peptide to be identified and/or sequenced, threading the protein or peptide into a nanopore of an identification or sequencing apparatus, moving the protein or peptide through the nanopore, and reading the sequence of the protein or peptide by means of electrical signals generated as the protein or nanopore passes between a gap in a pair of electrodes. In such embodiments, the polymer may be a peptide. To that end, the moving step may be established at least in part via the molecular motor.

In addition, in such method embodiments, the peptide incorporates a targeting motif for threading a molecular motor, and the peptide or protein may be pulled through the nanopore by the molecular motor protein.

In some embodiments, an apparatus for sequencing a polymer is provided which may comprise a support structure, a nanopore having a diameter of between about 1 to about 10 nm cut or otherwise provided into the support, a plurality of electrodes proximate to the nanopore for effecting current flow through each residue in the polymer as it passes through the pore, the current flow comprising one or more current signals, biasing means for applying a voltage across the electrodes, current detecting means for detecting the current signals, and a molecular motor arranged so as to pull the polymer through the nanopore.

In some embodiments, the threader molecule (polyionic) comprises a chemical concatenation of one protein or peptide with another protein or peptide. For example, in one embodiment, a polyionic threader molecule comprises a chemical concatenation of one or more peptides, where the peptides comprise an amino acid sequence that does not fold and contains a sufficient number of, for example, at least more than one amino acid residues that are charged at neutral pH or at a pH compatible with recognition tunneling readout, for example, pH ranging from about 3.0 to about 8.0. In one embodiment, the peptides used in chemical concatenation comprise at least 1, 2, 3, 5, 10, 15, 20, 25, 30, 40, 50, 60, or more amino acid residues that are naturally charged at neutral pH or at a pH suitable for recognition tunneling readout, for example, pH ranging from about 3.0 to about 8.0.

In some embodiments, the polyionic threader molecule comprises a chemical concatenation of a peptide comprising amino acid sequence GGSSGGSGGSGSSGD (SEQ ID NO: 1). That is, in these embodiments, the polyionic threader molecule comprises multiple, for example, 2, 3, 4, 5, 6, 7, 8, 10, 15, or 20 repeats of the amino acid sequence GGSSGGSGGSGSSGD (SEQ ID NO: 1). In some embodiments, the sequence of amino acids in GGSSGGSGGSGSSGD (SEQ ID NO: 1) may be varied. For example, in one embodiment, the sequence may be GGSGGSGSSGGSSGD (SEQ ID NO: 2). GGSGGSSGGSGSSGD (SEQ ID NO: 3), etc.

In some embodiments, the polyionic threader molecule comprises a chemical concatenation of a protein or peptide conjugated at the N terminus with a peptide through the natural amide bond for use in a recognition tunneling apparatus is provided, where the peptide may be disordered and carries one or more charged residues in the pH range of about 3 to about 8, and the peptide may be conjugated with an amino acid sequence for threading a molecular motor.

For example, in some embodiments, the polyionic threader molecule comprising a chemical concatenation of one or more peptides may comprise a special amino acid sequence at one end where the special amino acid sequence acts as a targeting/docking sequence or motif for binding to a molecular motor that will pull the sequencing complex through a nanopore. In one embodiment, the targeting sequence may comprise amino acid sequence AANDENYALLA (SEQ ID NO: 4) disclosed in Nivala et al.

In some embodiments, an apparatus for sequencing a polymer is provided and may comprise a support structure (which may comprise a membrane), a nanopore having a diameter of about 1 to about 10 nm cut into the structure, a plurality of electrodes proximate to the nanopore for sensing current flow through each residue in the polymer as it passes through the pore, and a molecular motor arranged so as to pull the polymer through the nanopore.

Many embodiments of the present disclosure become even more clear with reference to the figures, a brief description of which follows, and detailed description of some embodiments below.

DETAILED DESCRIPTION OF SOME OF THE EMBODIMENTS

Figure 1:
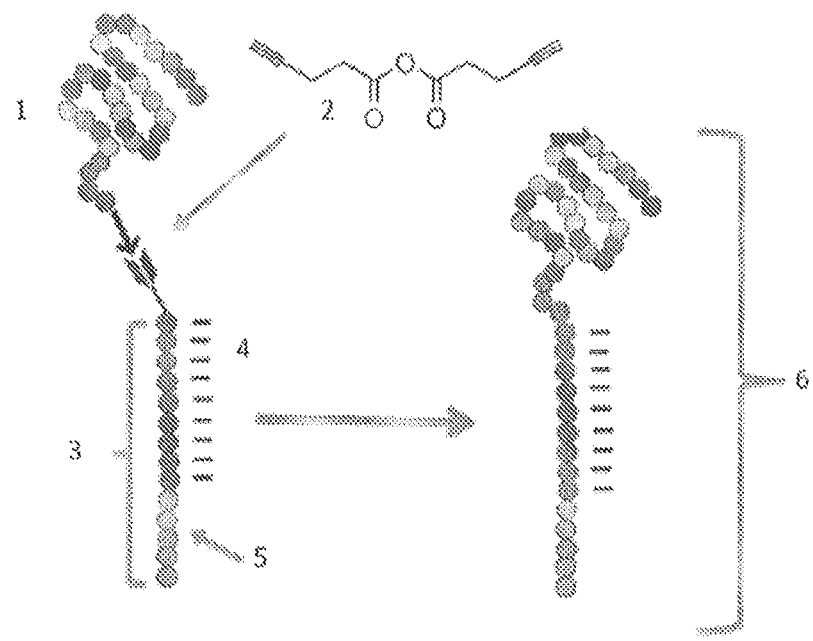
FIG. 1 illustrates the coupling of a protein or peptide to be sequenced to a threader molecule, according to some embodiments of the present disclosure.
Figure 2:
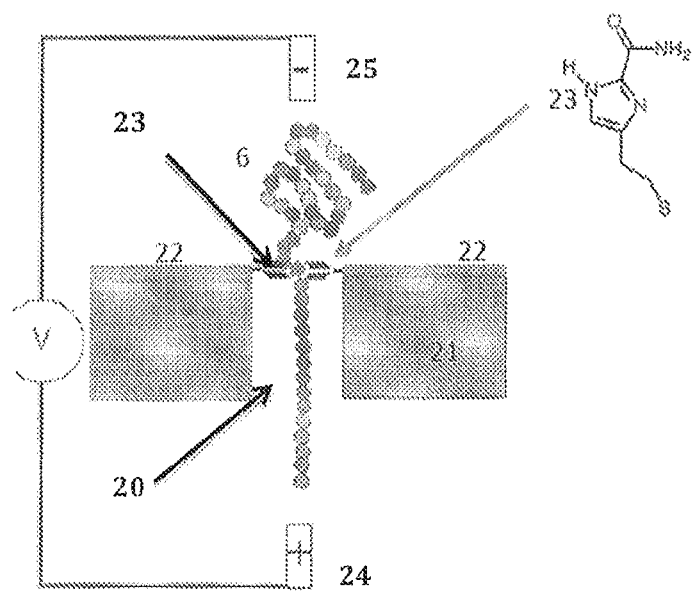
FIG. 2 illustrates use of a charged threader molecule to force (e.g., pull) a protein or peptide into a nanopore (e.g., contact with) of a recognition tunneling apparatus that incorporates reading electrodes, according to some embodiments of the present disclosure.
Figure 3:
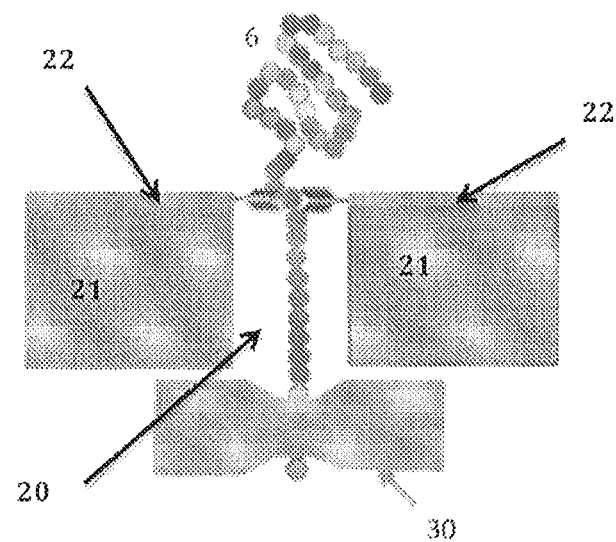
FIG. 3 illustrates a spontaneous threading of a molecular motor by a targeting sequence on the threader molecule, according to some embodiments of the present disclosure.

Before some embodiments of the present disclosure are described in detail, it is to be understood that such embodiments are not limited to particular variations set forth and may, of course, vary. Various changes may be made to embodiments described and equivalents may be substituted without departing from the true spirit and scope of inventions disclosed herein. In addition, many modifications may be made to adapt a particular situation, material, composition of matter, process, process act(s) or step(s), to the objective(s), spirit or scope of the present disclosure. All such modifications are intended to be within the scope of any and all claims supported by the present disclosure.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within embodiments of the disclosure. Also, it is contemplated that any optional feature of one and/or another of the disclosed embodiments described herein may be set forth and claimed independently, or in combination with any one or more of the features described herein.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

In some embodiments, the following reaction is provided for enabling recognition tunneling to achieve sequencing of one or more unknown proteins.

First, Pentynoic Anhydride (see Scheme 1, below) is dissolved in acetonitrile to a concentration of 1 mM, and a peptide to be sequenced is dissolved in acetate buffer. The pH of the peptide/acetate solution is adjusted to between about 5.0 and about 7.6. In some embodiments, the pH for the peptide/acetate solution is adjusted to about 5.5. The two solutions are preferably held at about 0° C., where they are mixed and maintained at about 0° C. for, in some embodiments, about 10 minutes to about 5 hours. In some embodiments, the two solutions are mixed and maintained at about 0° C. for about two (2) hours.

In some embodiments, the starting peptide is converted to a peptide modified with alkyne at its N-terminus as shown in Scheme 1 without any modifications on the primary amines of the lysine side chains.

Alkynylation of the N terminus of a peptide (i.e., the wavy line on product at right—the terminal unmodified lysine is shown) may be completed, for example, by reacting with pentynoic anhydride (above arrow, 2 in FIG. 1). The chemistry was tested on the peptide shown on the left.

In some embodiments, a faster reaction can occur if bromoacetic acid is used rather than pentynoic anhydride (see Scheme 2, below). The product is a peptide with a bromo-acetylated —N terminus, which may be readily coupled to a polyionic threader molecule by reaction with a thiol. In such embodiments, the reaction can be completed in about 20 minutes, using (for example) the conditions described above.

Scheme 2:

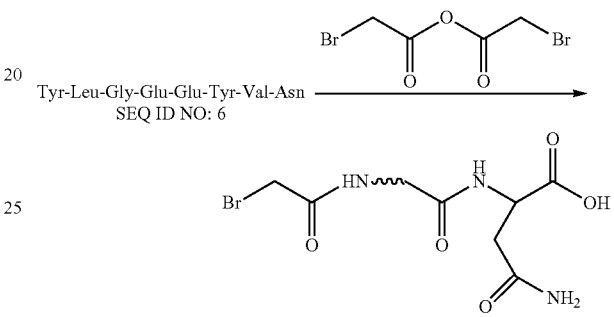

Tyr-Leu-Gly-Glu-Glu-Tyr-Val-Asn
SEQ ID NO: 6

Bromo acetylation of the N terminus of any peptide (i.e., the wavy line on product at right—the terminal unmodified lysine is shown) may be completed, for example, by reacting with bromoacetyl anhydride (above arrow).

A protein or peptide to be sequenced, once modified as described above, can be attached or linked to a polyionic therader molecule. In some embodiments, it may be advantageous to use a charged peptide as the polyionic threader molecule (see Nivala et al.).[1] In particular, in some embodiments, the threader molecule can be synthesized to contain a reactive group (e.g., such as an azide or thiol) at one end to bind to the protein/peptide to be sequenced, and a targeting motif, such as a peptide sequence, designed to bind a molecular motor (protein motor, for example) that can be used to pull the protein through a nanopore (see Id., Nivala et al.). In some embodiments, in the case of the ClpX motor used by Nivala et al., the targeting motif for threading the molecular motor is AANDENYALLA (SEQ ID NO: 4), for example. The polyionic component of the threader molecule can be any non-folding sequence that contains a number of charged residues. For example, the sequence used by Nivala et al. was:

Scheme 1:

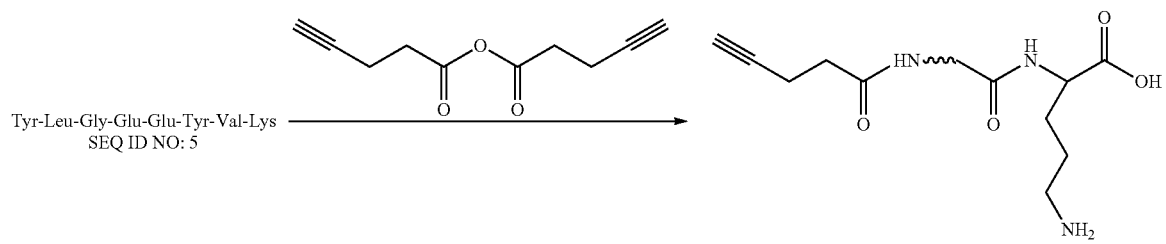

Tyr-Leu-Gly-Glu-Glu-Tyr-Val-Lys
SEQ ID NO: 5

```
                                               (SEQ ID NO: 7)
       GGSSGGSGGSGSSGDGGSSGGSGGSGSSG

DGGSSGGSGGDGSSGDGGSDGDSDGSDGD

GDSDGDD
```

The 10 aspartic acid residues are negatively charged at neutral pH and provide the charge that can be used to drag this tail into the nanopore.

In some embodiments, the threader molecule comprises the following sequence comprising the polyionic component and the targeting motif shown above:

```
                                               (SEQ ID NO: 8)
       GGSSGGSGGSGSSGDGGSSGGSGGSGSSG

DGGSSGGSGGDGSSGDGGSDGDSDGSDGD

GDSDGDDAANDENYALAA
```

In some embodiments, a standard solid phase peptide synthesis can be used to place an azide at the end of GGSSGGSGGSGSSGDGGSSGGSGGSGSS GDGGSSGGSGGDGSSGDGGSDGDSDGSDGDGDS-DGDDAANDENYALAA (SEQ ID NO: 8) 3 to form a standard (I) reagent, such as a polyionic threader molecule, for binding to a protein containing a reactive group, such as an alkyne or a bromoacetyl group, using the click chemistry described above (for example). Note that, because the threader molecule (I) does not contain any lysines, no special reaction conditions are required to produce this threader molecule (according to some embodiments).

```
       I- an azide containing threading peptide
                                               (SEQ ID NO: 9)
       N3GGSSGGSGGSGSSGDGGSSGGSGGSGSS

GDGGSSGGSGGDGSSGDGGSDGDSDGSDG

DGDSDGDDAANDENYALAA
```

I—an azide containing threading peptide

In some embodiments of the present disclosure, the azide (N₃) containing peptide I is coupled to the alkyne terminated "unknown" protein or peptide as modified with an alkyne (e.g., Scheme 1).

Alternatively, in some embodiments, the peptide can be synthesized with a cysteine residue at the N terminus (II):

```
       II- a cysteine terminated threading peptide
                                              (SEQ ID NO: 10)
       CGGSSGGSGGSGSSGDGGSSGGSGGSGSS

GDGGSSGGSGGDGSSGDGGSDGDSDGSDG

DGDSDGDDAANDENYALAA
```

II—a cysteine terminated threading peptide

This peptide (II), in some embodiments, can be readily coupled to the bromine terminated "unknown" protein or peptide (e.g., Scheme 2).

Thus, according to some embodiments, a charged polyionic tail is readily ligated to an unknown protein. In particular, peptides carrying charge and sequences that assemble onto a molecular motor may be readily coupled to the N terminus of any protein or peptide that has an exposed N terminus.

EXAMPLE

Sequencing a Protein of Unknown Composition

Referring to FIGS. 1-5, the workflow for a single-molecule protein sequencing run, according to some embodiments, is described. For example, in FIG. 1, an unknown protein 1 is dissolved into aqueous acetate buffer, adjusted to a pH of between about 5.0 and about 7.6, but preferably, in some embodiments, to a pH of about 5.5. Pentynoic Anhydride (e.g., see Scheme 1 and inset in FIG. 1) is dissolved in acetonitrile to a concentration of about 1 mM, in some embodiments, but this can be between about 10 nM and about 100 mM (for example). The two solutions, held at about 0° C., for example, are mixed and maintained at about 0° C. for about 10 minutes to about 5 hours, but preferably, in some embodiments, to about 2 hours. The result, in some embodiments, is the addition of a reactive alkyne group (symbolized by the arrow head comprising 2 at the N terminus of the protein but not at other sites. It will be appreciated by one of skill in the art, that, according to some embodiments, the same process can be carried out using peptides obtained from the unknown protein by a Trypsin digest. Such a digest may be essential in cases where the N-terminus of the protein is buried in the body of the protein, thereby making it unaccessible to the Pentynoic Anhydride without a digest. The protein, 1, thus modified may then be coupled to reactive end of a threader molecule 3. This reactive end may be an azide group or a thiol. The result is the coupled system of unknown protein and threader molecule 6.

In some embodiments, the threader molecule can consist of two parts. For example, the first part 4 (polyionic component) is a charged peptide that does not fold into a fixed secondary structure, for example the sequence:

```
                                              (SEQ ID NO: 11)
       GGSSGGSGGSGSSGDGGSSGGSGGSGSSG

DGGSSGGSGGDGSSGDGGSDGDSDGSDGD

GDSDGDD
```

Note, the N terminus of the sequence shown is modified (for example) to contain an azide or a thiol.

The second part 5 may be a sequence (targeting motif) designed to thread the molecular motor. In the case of ClpX, this may be an 11 aa ClpX targeting motif: AANDENYA-LAA (SEQ ID NO: 4). It will be appreciated by one of skill in the art that the same ends can be achieved using the thiol-bromo reaction described in Scheme 2 (for example).

Once the complex 6 is formed, it can be dissolved into a suitable salt solution, e.g., KCl, NaCl or any other mono or divalent salt such as $MgCl_2$ included in the solution if required for the operation of a molecular motor, at concentrations from about 1 mM to about 1M. Accordingly, once in the salt solution, molecules can then be drawn into a nanopore 20 (provided on e.g., substrate 21) using electrophoresis as shown in the recognition tunneling apparatus shown in FIG. 2. For example, if the charges on the threader molecule are negative, then the molecules will be pulled into the pore by using a bias applied between a positive reference electrode 25 on the input side of the pore 20 and the negative reference electrode 24. If the protein or peptide 6 is folded, it will stop at the entrance to the pore, so long as, in some embodiments, the applied bias V is small. Suitable values may include 5 mV to 500 mV.

In some embodiments, the nanopore may be modified to have a pair of electrodes 22 accessible to the amino acid residues. In some embodiments, these electrodes may be Pd or Pt with a gap of between about 2 to about 4 nm, as described in pending PCT application no. PCT/US2013/032240, the entire disclosure of which is herein incorporated by reference. The electrodes may be functionalized with reader molecules 23 that strongly bind to the metal and form transient, non-covalent contacts with the target amino acid residues. In some embodiments, the molecule may be the imidazole carboxamide shown inset in FIG. 2 (for example).

Accordingly, with the protein or peptide 6 stalled in this position, and about 1 nM to about 1 mM (but in some embodiments about 100 nM) ClpX (or other motor protein) 30 introduced into the output side of the nanopore (FIG. 3), the motor protein threads the motor targeting motif (5 in FIG. 1).

Figure 4:
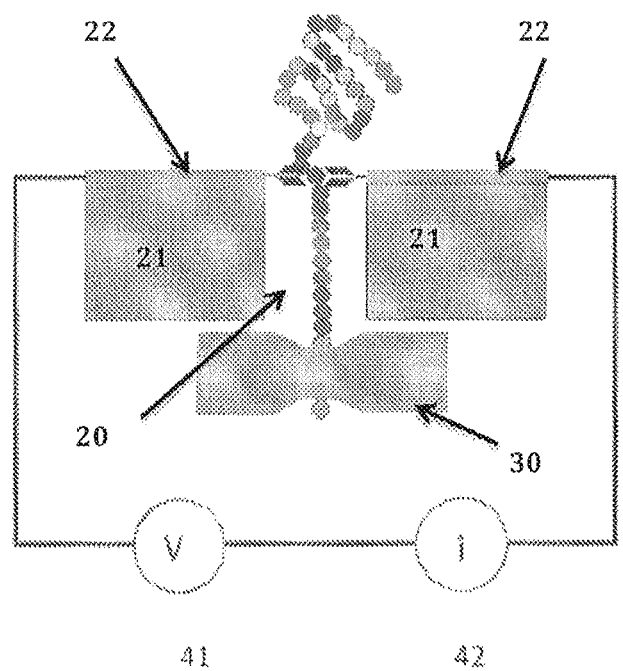
FIG. 4 illustrates a biasing arrangement for reading a recognition tunneling signal from each amino acid residue in a recognition tunneling apparatus (for example), according to some embodiments of the present disclosure.

Referring to FIG. 4, a bias V applied via biasing means 41 may be applied across the junction while the current through the molecular complex in the junction is read/determined by current monitor 42. This current signal may be used to identify the amino acid residue in the gap, e.g., as described in PCT application no. PCT/US2013/024130, entitled, "Systems, Apparatuses and Methods for Reading an Amino Acid Sequence," the entire disclosure of which is herein incorporated by reference.

Figure 5:
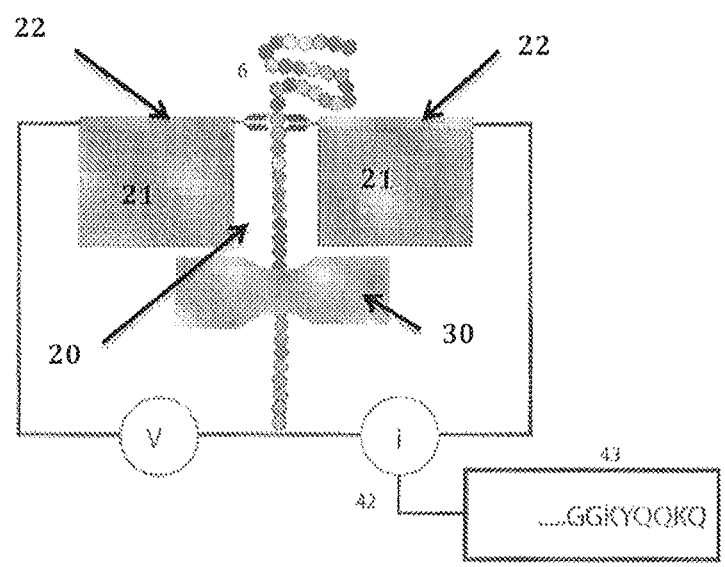
FIG. 5 illustrates the reading out of a sequence of a protein/peptide (SEQ ID NO: 12) as the molecular motor forces (e.g., pulls) a threader and protein or peptide through the nanopore, according to some embodiments of the disclosure.

In some embodiments, when ATP (for example) is added to the solution on the output side (e.g., at a concentration of about 1 nM to about 100 mM, but preferably about 1 mM) the motor begins to pull the protein or peptide through the tunnel gap, one residue at a time (for example), as shown in FIG. 5, resulting is a readout/determination of the sequence by means of a computer 43, for example, that determines the characteristic current signals detected by current monitor 42, generated as each residue in turn is trapped in the gap, by, for example, comparing the detected signals against a database of polymer signal signatures (bias means 41, as well as other sensors, devices, databases, and the like, may be in communication or otherwise connected to computer 43).

Any and all references to publications or other documents, including but not limited to, patents, patent applications, articles, webpages, books, etc., presented in the present application, are herein incorporated by reference in their entirety, except insofar as the subject matter may conflict with that of the embodiments of the present disclosure (in which case what is present herein shall prevail). The referenced items are provided solely for their disclosure prior to the filing date of the present application. Nothing herein is to be construed as an admission that any invention disclosed herein is not entitled to antedate such material by virtue of prior invention.

Although example embodiments of the devices, systems and methods have been described herein, other modifications are possible. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. In addition, any logic flow depicted in the above disclosure and/or accompanying figures may not require the particular order shown, or sequential order, to achieve desirable results. Moreover, embodiments of the subject disclosure may include methods, systems and devices which may further include any and all elements from any other disclosed methods, systems, and devices, including any and all elements corresponding to polymer translocation. In other words, elements from one and/or another disclosed embodiment may be interchangeable with elements from other disclosed embodiments. In addition, one or more features/elements of disclosed embodiments may be removed and still result in patentable subject matter (and thus, resulting in yet more embodiments of the subject disclosure). In addition, some embodiments of the present disclosure are distinguishable from the prior art for expressly not requiring one and/or another features disclosed in the prior art (e.g., some embodiments may include negative limitations). Other implementations of some of the embodiments disclosed herein are within the scope of at least some of the following claims of the numerous claims which are supported by the present disclosure which may be presented.

REFERENCES

Herein Incorporated by Reference in their Entireties

1 Nivala, J., Marks, D. B. & Akeson, M. Unfoldase-mediated protein translocation though an alpha-hemolysin pore. *Nature Biotechnol.* doi: 10.138/nbt.2503 (2013).
2 Rodriguez-Larrea, D. & Bayley, H. Multistep protein unfolding during nanopore translocation. *Nature Nanotechnology* 8, 288-295 (2013).
3 Kolb, H. C., Finn, M. G. & Sharpless, K. B. Click Chemistry: Diverse Chemical Function from a Few Good Reactions. *Angew. Chem. Int. Ed.* 40, 2004-2021 (2001).
4 Hall, A. R. et al. Hybrid pore formation by directed insertion of alpha hemolysin into solid-state nanopores. *Nature Nanotechnology* 5, 874-877 (2010).

What is currently claimed:

1. A method, comprising:
   attaching a polymer containing one or more charged residues to only an N terminus of a protein or peptide to be identified and/or sequenced to generate a modified protein or peptide, wherein the rest of the protein or peptide remains unmodified;
   applying a voltage or an electric current to thread the modified protein or peptide into a nanopore of an identification or sequencing apparatus, the polymer containing one or more charged residues of the modified protein or peptide being pulled into the nanopore before the rest of the modified protein or peptide;
   moving the modified protein or peptide through the nanopore; and
   reading the sequence of the protein or peptide by means of electrical signals generated as the modified protein or peptide passes between a gap in a pair of electrodes.

2. The method of claim 1, wherein the polymer is a peptide.

3. The method of claim 1, wherein moving is established at least in part via a molecular motor.

4. The method of claim 2, wherein the peptide incorporates a targeting motif for threading a molecular motor.

5. The method of claim 1, further comprising attaching a reactive alkyne group at the N terminus of the protein or peptide prior to the attachment of the polymer containing one or more charged residues.

6. The method of claim 1, further comprising attaching a bromoacetyl group at the N terminus of the protein or peptide prior to the attachment of the polymer containing one or more charged residues.

7. The method of claim 1, the one or more charged residues being in a pH range from about 3 to about 8.

* * * * *

SEQUENCE LISTING

<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: threader molecule polyionic component monomer

<400> SEQUENCE: 1

Gly Gly Ser Ser Gly Gly Ser Gly Gly Ser Gly Ser Ser Gly Asp
1               5                   10                  15

-continued

<210> SEQ ID NO 2
<211> LENGTH: 15
<212> TYPE: PRT
<213> ORGANISM: Artificial Sequence
<220> FEATURE:
<223> OTHER INFORMATION: threader molecule polyionic component monomer

<400> SEQUENCE: 2

Gly Gly Ser Gly Gly Ser Gly Ser Ser Gly Gly Ser Ser Gly Asp
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: threader molecule polyionic component monomer

<400> SEQUENCE: 3

Gly Gly Ser Gly Gly Ser Ser Gly Gly Ser Gly Ser Ser Gly Asp
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: molecular motor targeting sequence

<400> SEQUENCE: 4

Ala Ala Asn Asp Glu Asn Tyr Ala Leu Leu Ala
1               5                   10

<210> SEQ ID NO 5
<211> LENGTH: 8
<212> TYPE: PRT
<213> ORGANISM: Artificial Sequence
<220> FEATURE:
<223> OTHER INFORMATION: starting peptide for alkyne modified peptide

<400> SEQUENCE: 5

Tyr Leu Gly Glu Glu Tyr Val Lys
1               5

<210> SEQ ID NO 6
<211> LENGTH: 8
<212> TYPE: PRT
<213> ORGANISM: Artificial Sequence
<220> FEATURE:
<223> OTHER INFORMATION: starting peptide for bromo-acetylated peptide

<400> SEQUENCE: 6

Tyr Leu Gly Glu Glu Tyr Val Asn
1               5

<210> SEQ ID NO 7
<211> LENGTH: 65
<212> TYPE: PRT
<213> ORGANISM: Artificial Sequence
<220> FEATURE:
<223> OTHER INFORMATION: threader molecule polyionic component

<400> SEQUENCE: 7

Gly Gly Ser Ser Gly Gly Ser Gly Gly Ser Gly Ser Ser Gly Asp Gly
1               5                   10                  15

Gly Ser Ser Gly Gly Ser Gly Gly Ser Gly Ser Ser Gly Asp Gly Gly

```
                20                  25                  30
Ser Ser Gly Gly Ser Gly Gly Asp Gly Ser Ser Gly Asp Gly Gly Ser
            35                  40                  45

Asp Gly Asp Ser Asp Gly Ser Asp Gly Asp Gly Ser Asp Gly Asp
        50                  55                  60

Asp
65

<210> SEQ ID NO 8
<211> LENGTH: 76
<212> TYPE: PRT
<213> ORGANISM: Artificial Sequence
<220> FEATURE:
<223> OTHER INFORMATION: threader molecule polyionic component and
      targeting motif

<400> SEQUENCE: 8

Gly Gly Ser Ser Gly Gly Ser Gly Gly Ser Gly Ser Ser Gly Asp Gly
1               5                   10                  15

Gly Ser Ser Gly Gly Ser Gly Gly Ser Gly Ser Ser Gly Asp Gly Gly
                20                  25                  30

Ser Ser Gly Gly Ser Gly Gly Asp Gly Ser Ser Gly Asp Gly Gly Ser
            35                  40                  45

Asp Gly Asp Ser Asp Gly Ser Asp Gly Asp Gly Ser Asp Gly Asp
        50                  55                  60

Asp Ser Ser Asn Asp Glu Asn Tyr Ala Leu Ala Ala
65                  70                  75

<210> SEQ ID NO 9
<211> LENGTH: 76
<212> TYPE: PRT
<213> ORGANISM: Artificial Sequence
<220> FEATURE:
<223> OTHER INFORMATION: azide containing threading peptide
<220> FEATURE:
<221> NAME/KEY: MISC_FEATURE
<222> LOCATION: (1)..(1)
<223> OTHER INFORMATION: May be modified with an azide

<400> SEQUENCE: 9

Gly Gly Ser Ser Gly Gly Ser Gly Gly Ser Gly Ser Ser Gly Asp Gly
1               5                   10                  15

Gly Ser Ser Gly Gly Ser Gly Gly Ser Gly Ser Ser Gly Asp Gly Gly
                20                  25                  30

Ser Ser Gly Gly Ser Gly Gly Asp Gly Ser Ser Gly Asp Gly Gly Ser
            35                  40                  45

Asp Gly Asp Ser Asp Gly Ser Asp Gly Asp Gly Ser Asp Gly Asp
        50                  55                  60

Asp Ser Ser Asn Asp Glu Asn Tyr Ala Leu Ala Ala
65                  70                  75

<210> SEQ ID NO 10
<211> LENGTH: 77
<212> TYPE: PRT
<213> ORGANISM: Artificial Sequence
<220> FEATURE:
<223> OTHER INFORMATION: cysteine terminated threading peptide

<400> SEQUENCE: 10

Cys Gly Gly Ser Ser Gly Gly Ser Gly Gly Ser Gly Ser Ser Gly Asp
1               5                   10                  15
```

```
Gly Gly Ser Ser Gly Gly Ser Gly Gly Ser Gly Ser Ser Gly Asp Gly
                20                  25                  30

Gly Ser Ser Gly Gly Ser Gly Gly Asp Gly Ser Ser Gly Asp Gly Gly
            35                  40                  45

Ser Asp Gly Asp Ser Asp Gly Ser Asp Gly Asp Gly Asp Ser Asp Gly
        50                  55                  60

Asp Asp Ser Ser Asn Asp Glu Asn Tyr Ala Leu Ala Ala
65                  70                  75

<210> SEQ ID NO 11
<211> LENGTH: 65
<212> TYPE: PRT
<213> ORGANISM: Artificial Sequence
<220> FEATURE:
<223> OTHER INFORMATION: threader molecule polyionic component

<400> SEQUENCE: 11

Gly Gly Ser Ser Gly Gly Ser Gly Gly Ser Gly Ser Ser Gly Asp Gly
1               5                   10                  15

Gly Ser Ser Gly Gly Ser Gly Gly Ser Gly Ser Ser Gly Asp Gly Gly
                20                  25                  30

Ser Ser Gly Gly Ser Gly Gly Asp Gly Ser Ser Gly Asp Gly Gly Ser
            35                  40                  45

Asp Gly Asp Ser Asp Gly Ser Asp Gly Asp Gly Asp Ser Asp Gly Asp
        50                  55                  60

Asp
65

<210> SEQ ID NO 12
<211> LENGTH: 8
<212> TYPE: PRT
<213> ORGANISM: Unknown
<220> FEATURE:
<223> OTHER INFORMATION: exemplary result of unknown composition
      sequencing

<400> SEQUENCE: 12

Gly Gly Lys Tyr Gln Gln Lys Gln
1               5
```